(12) United States Patent
Guckel et al.

(10) Patent No.: US 7,592,293 B2
(45) Date of Patent: *Sep. 22, 2009

(54) METHOD FOR PRODUCING A MULTI-LAYER CATALYST FOR OBTAINING PHTHALIC ANHYDRIDE

(75) Inventors: Christian Guckel, Paramus, NJ (US); Harald Dialer, Munich (DE); Marvin Estenfelder, Karlsruhe (DE); Werner Pitschi, Bruckmuhl (DE)

(73) Assignee: Sud-Chemie AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/817,362

(22) Filed: Aug. 29, 2007

(65) Prior Publication Data

US 2008/0194844 A1 Aug. 14, 2008

(30) Foreign Application Priority Data

Mar. 2, 2005 (DE) .................. 10 2005 009 472

(51) Int. Cl.
*B01J 21/06* (2006.01)
*C07D 307/89* (2006.01)

(52) U.S. Cl. .................. 502/350; 502/20; 502/242; 549/248; 549/249

(58) Field of Classification Search ............... 549/248, 549/249; 502/20, 350, 242
See application file for complete search history.

(56) References Cited

U.S. PATENT DOCUMENTS

| | | | |
|---|---|---|---|
| 2,035,606 A | 3/1936 | Jaeger | |
| 2,142,678 A * | 1/1939 | Porter | 549/248 |
| 3,684,741 A | 8/1972 | Friedrichsen | |
| 3,799,886 A | 3/1974 | Felice | |
| 3,830,755 A | 8/1974 | Reuter | |
| 3,926,846 A | 12/1975 | Ono | |
| 4,405,505 A | 9/1983 | Neri | |
| 4,489,204 A * | 12/1984 | Neri et al. | 549/248 |
| 5,235,071 A * | 8/1993 | Ueda et al. | 549/248 |
| 5,677,261 A | 10/1997 | Tenten | |
| 5,792,719 A | 8/1998 | Eberle | |
| 5,969,160 A | 10/1999 | Lindstrom | |
| 6,288,273 B1 | 9/2001 | Heidemann | |
| 6,362,345 B1 | 3/2002 | Heidemann | |
| 6,458,970 B1 | 10/2002 | Hefele | |
| 6,586,361 B1 | 7/2003 | Heidemann | |
| 6,700,000 B1 | 3/2004 | Heidemann | |
| 6,774,246 B2 | 8/2004 | Reuter | |
| 7,151,184 B2 | 12/2006 | Storck | |
| 7,390,911 B2 * | 6/2008 | Neto et al. | 549/249 |
| 2006/0276661 A1 | 12/2006 | Storck | |
| 2007/0060758 A1 | 3/2007 | Storck | |
| 2007/0066836 A1 | 3/2007 | Neto | |
| 2007/0093384 A1 | 4/2007 | Storck | |
| 2008/0064594 A1 | 3/2008 | Neto | |

FOREIGN PATENT DOCUMENTS

| | | |
|---|---|---|
| DE | 1642938 | 5/1971 |
| DE | 2005969 | 8/1971 |
| DE | 19709589 | 9/1998 |
| DE | 102004026471 | 12/2005 |
| EP | 0099431 A1 | 2/1984 |
| EP | 0286448 | 10/1988 |
| EP | 0522871 | 1/1993 |
| EP | 0676400 | 4/1995 |
| EP | 0985648 | 3/2000 |
| GB | 2298197 A | 8/1996 |
| WO | 2005115615 | 12/2005 |
| WO | 2005115616 | 12/2005 |

OTHER PUBLICATIONS

Sadhukan et al, AIChE Journal, vol. 22, No. 4, p. 808-810 (1976).*
English translation of International Preliminary Report on Patentability pertaining to International application No. PCT/EP2005/012703. See reference to U.S. Appl. No. 11/914,147 in the Information Disclosure Statement filed on Jan. 7, 2008.
English translation of International Preliminary Report on Patentability pertaining to international application No. PCT/EP2006/001915. See reference to U.S. Appl. No. 11/817,428 in the Information Disclosure Statement filed on Jan. 7, 2008. This application may contain information material to the patentability of the current application.
Towae, et al., "Phthalic Acid and Derivatives", Ullmann's Encyclopedia of Industrial Chemistry, vol. A20, 1992, pp. 181-211.
Office Action dated Mar. 9, 2009 with respect to U.S. Appl. No. 11/575,789.
Office Action dated Mar. 10, 2009 with respect to U.S. Appl. No. 11/817,428.
Response filed May 27, 2009 to Office Action dated Mar. 9, 2009 with respect to U.S. Appl. No. 11/575,789, a "potentially related" application disclosed in an Information Disclosure Statement filed on Jan. 7, 2008.
Response filed May 20, 2009 to Office Action dated Mar. 10, 2009 with respect to U.S. Appl. No. 11/817,428, a "potentially related" application disclosed in an Information Disclosure Statement filed on Jan. 7, 2008.

* cited by examiner

*Primary Examiner*—Bernard Dentz
(74) *Attorney, Agent, or Firm*—Scott R. Cox

(57) ABSTRACT

The present invention relates to processes for improving or optimizing a catalyst for the preparation of phthalic anhydride by gas-phase oxidation of o-xylene and/or naphthalene, which comprises the following steps: a) provision of a starting catalyst (C) comprising at least one first catalyst zone located towards the gas inlet and a second catalyst zone located closer to the gas outlet, with the catalyst zones preferably each having an active composition comprising $TiO_2$; b) replacement of part of the first catalyst zone by an upstream zone of a catalyst having a higher activity than the first catalyst zone in order to provide an improved catalyst. Furthermore, an improved catalyst obtainable by this process is described.

25 Claims, No Drawings

METHOD FOR PRODUCING A MULTI-LAYER CATALYST FOR OBTAINING PHTHALIC ANHYDRIDE

The invention relates to a process for producing a catalyst or for improving or optimizing a catalyst for the preparation of phthalic anhydride by gas-phase oxidation of o-xylene and/or naphthalene and also an improved catalyst which can be obtained by this process.

The industrial production of phthalic anhydride is carried out by catalytic gas-phase oxidation of o-xylene and/or naphthalene. For this purpose, a catalyst suitable for the reaction is installed in a reactor, preferably a shell-and-tube reactor in which a multiplicity of tubes are arranged in parallel, and a mixture of the hydrocarbon(s) and an oxygen-containing gas, for example air, is passed through it from above or below. Owing to the evolution of a large amount of heat in such oxidation reactions, it is necessary for a heat-transfer medium to be passed around the reaction tubes and thus remove the heat evolved so as to avoid hot spots. This energy can be utilized for the production of steam. The heat-transfer medium used is generally a salt melt, preferably a eutectic mixture of $NaNO_2$ and $KNO_3$.

Multizone (multi-layer) catalyst systems are used nowadays for the oxidation of o-xylene and/or naphthalene to phthalic anhydride. The objective is to match the activity of the individual catalyst zones to the progress of the reaction along the reactor axis. This makes it possible to achieve a high yield of the desired product PA and at the same time to obtain a very low yield of the undesirable intermediate phthalide. The 1st zone (=the zone closest to the reactor inlet) usually has the lowest activity, since the highest starting material concentrations and thus the highest reaction rates occur in the region near the reactor inlet. The heat liberated in the chemical reaction heats the reaction gas up to the point at which the energy produced by the reaction is just equal to the energy passed to the coolant. This hottest point in the reaction tube is referred to as the hot spot. An excessively high activity in the 1st zone would lead to an uncontrolled increase in the hot spot temperature which usually leads to a reduction in selectivity and can even lead to a runaway reaction.

A further important aspect which has to be taken into account in the design of the activity of the individual catalyst zones is the position of the hot spot in the 1st catalyst zone. Since the catalyst activity decreases with increasing time of operation, the position of the hot spot moves ever further in the direction of the reactor outlet. This can even continue so far that the hot spot migrates from the 1st zone into the 2nd zone or even into an even later zone. The associated significantly reduced PA yield frequently makes it necessary in such a case for the catalyst to be replaced, which leads to high production downtimes.

EP 1 084 115 B1 describes a multizone catalyst for the oxidation of o-xylene and/or naphthalene to phthalic anhydride, in which the activity of the individual catalyst zones increases continuously from the reactor inlet to the reactor outlet. This is achieved by increasing the amount of active composition and at the same time decreasing the alkali metal content of the catalyst so that the catalyst zone directly at the catalyst inlet has the lowest active composition content and the highest alkali metal content.

DE 103 23 818 A1 describes a multizone catalyst for the oxidation of o-xylene and/or naphthalene to phthalic anhydride which comprises at least three successive zones, in which the activity of the individual catalyst zones increases continuously from the reactor inlet to the reactor outlet. This is achieved by use of $TiO_2$ having a differing BET surface area so that the BET surface area of the $TiO_2$ used in the zone at the reactor inlet is lower than that in the subsequent zones and is highest in the last zone (reactor outlet).

DE 103 23 461 A1 describes a multizone catalyst for the oxidation of o-xylene and/or naphthalene to phthalic anhydride, in which the activity of the individual catalyst zones increases from the reactor inlet to the reactor outlet, with the ratio of $V_2O_5$ to $Sb_2O_3$ in the 1st zone being from 3.5:1 to 5:1.

DE 103 23 817 A1 describes a multizone catalyst for the oxidation of o-xylene and/or naphthalene to phthalic anhydride which comprises at least three successive zones, in which the activity of the individual catalyst zones increases continuously from the reactor inlet to the reactor outlet and the last zone closest to the reactor outlet contains more than 10% by weight of $V_2O_5$ and is the only zone in which P is present.

A disadvantage of the catalysts described there is that despite the use of such structured catalysts, the life of the catalyst is not satisfactory, especially in respect of the increasing migration of the hot spot in the direction of the gas stream. Positioning of the hot spot in the (most active) catalyst zone further towards the gas outlet also restricts the ability to achieve fine adjustment of the selectivity of the catalyst so as to avoid undesirable by-products.

There is therefore a continuing need for improved multizone catalysts for the preparation of phthalic anhydride and other products obtained by partial oxidation of hydrocarbons.

It was therefore an object of the present invention to provide a process for producing an improved catalyst for the preparation of phthalic anhydride by gas-phase oxidation of o-xylene and/or naphthalene, which avoids the disadvantages of the prior art and, in particular, makes advantageous positioning of the hot spot and a longer life of the improved catalyst possible. A particular objective of the present invention is to bring about an increase in the catalyst life at a product yield which is the same or even improved.

According to a first aspect of the invention, this object is achieved by the process according to Claim 1. Preferred embodiments are indicated in the subordinate claims.

It has surprisingly been found that the object of the invention can be achieved by replacing part of the first catalyst zone nearest the gas inlet in conventional catalysts having two or more catalyst zones (starting catalysts) by an upstream zone of a catalyst having a higher activity than the first catalyst zone of the starting catalyst. As a result, the remaining part of the first catalyst zone of the starting catalyst becomes the second catalyst zone in the improved catalyst. This upstream catalyst zone which is located directly at the reactor inlet and has a higher activity than the subsequent second catalyst zone (formerly the first catalyst zone in the starting catalyst) significantly increases the reaction rate in a comparatively short region at the reactor inlet in which, owing to the low temperature, only low reaction rates and thus low chemical conversions usually occur. This finally results in earlier positioning of the hot spot closer to the reactor inlet than without the upstream catalyst zone according to the invention. This is advantageous in respect of a long life (operating life) as described above and also makes better fine adjustment of the catalyst selectivity in the catalyst sections located downstream of the abovementioned hot spot in the direction of the gas outlet possible. Both yield and selectivity can be increased in this way.

According to a first aspect, the present invention thus provides a process for improving or optimizing a catalyst for the preparation of phthalic anhydride by gas-phase oxidation of o-xylene and/or naphthalene, which comprises the following steps:

a) provision of a starting catalyst (C) comprising at least one first catalyst zone located towards the gas inlet and a second catalyst zone located closer to the gas outlet, with the catalyst zones being able to have different compositions and preferably each having an active composition comprising $TiO_2$, b) replacement of part of the first catalyst zone by an upstream zone of a catalyst having a higher activity than the (formerly) first catalyst zone in order to provide an improved catalyst.

As starting catalyst, it is thus possible to use any catalyst for the partial oxidation of hydrogens, in particular for the preparation of phthalic anhydride by gas-phase oxidation of o-xylene and/or naphthalene, which has been described in the prior art and has at least two catalyst zones. For example reference may here be made to the catalyst systems as described in DE 10 2004 026 472.4 and DE 10 2004 026 471.6 of the same applicant or in the abovementioned EP 1 084 115 A1, DE 103 23 818 A1, DE 103 23 461 A1, DE 103 23 817 A1. However, other catalysts which are known to those skilled in the art from the prior art and have at least two different catalyst zones can likewise be used as starting catalyst compositions for producing the improved catalysts of the invention. In the two-zone or multizone PA catalysts of the prior art, the catalyst activity generally increases from zone to zone from the gas inlet to the gas outlet. Accordingly, the hot spot should be positioned in the first, least active catalyst zone (which at the same time has a high selectivity). According to the invention, the catalyst zones preferably have different compositions, with the catalyst zones (in particular the upstream catalyst zone and the second catalyst zone of the improved catalyst) also being able, for example, to differ only in that they have a different active composition content (e.g. based on a particular reactor volume).

According to a preferred embodiment of the process of the invention, the position of the temperature maximum (hot spot) in the first catalyst zone is determined under the normal (envisaged in the prior art) operating conditions of the catalyst (starting catalyst). This position of the hot spot, expressed as the distance of the hot spot in the first catalyst zone from the beginning of the catalyst bed (at the gas inlet end of the reactor), can be denoted as A and in many catalyst systems of the prior art is from 60 to 120 cm, in particular from 70 to 100 cm. In the process of the invention, preference is given to replacing only that part of the first catalyst zone of the starting catalyst which is shorter than the distance A determined for the starting catalyst. The intention of this is to avoid a situation in which the hot spot is located in the more active upstream catalyst zone in the improved catalyst. Rather, the hot spot in the improved catalyst is preferably located in the second catalyst zone, corresponding to the first catalyst zone of the starting catalyst. It has surprisingly been found that the use of the upstream more active catalyst zone makes it possible to achieve a reduction in the distance A, i.e. the hot spot is located closer to the gas inlet than in the original starting catalyst. The associated improvement in the life and the performance of the catalyst have been mentioned above.

In a preferred embodiment according to the invention, from about 5 to about 60% of the length of the first catalyst zone of the starting catalyst is replaced by the upstream catalyst zone. Preference is given to replacing from about 10 to 50% of the first catalyst zone, calculated from the beginning of the catalyst bed at the gas inlet end.

The length of the upstream catalyst zone based on the above-described distance A in the starting catalyst is from about 0.1·A to 0.9·A, particularly preferably from about 0.2·A to 0.8·A.

As a result, it is generally possible to ensure advantageous positioning of the hot spot close to the gas inlet end of the improved catalyst, but preferably in the second (less active) catalyst zone.

In a more preferred embodiment according to the invention, the length of the upstream catalyst zone is from 5 to 25%, particularly preferably from 10 to 25% of the total length of the catalyst bed of the improved catalyst. In addition to other factors, the height of the axial temperature gradient in the surrounding cooling medium also plays a role in the design of the length. In any case, the length of the upstream catalyst zone is less than would correspond to the position of a conceptual hot spot, measured as the distance from the beginning of the catalyst bed to the point at which the maximum temperature is achieved, which would be formed if, in place of the upstream zone, the corresponding region were also to be filled with catalyst of the second zone (corresponding to the catalyst of the first zone of the starting catalyst). According to a particularly preferred embodiment, the ratio of the length of the upstream catalyst zone to the length of the second catalyst zone is less than or equal to 0.9. This ratio is more preferably in the range from about 0.1 to 0.9, in particular from 0.1 to 0.7, preferably from 0.15 to 0.5. This ensures that the first zone is not too long compared to the second zone in which the hot spot is preferably located.

In a preferred embodiment according to the invention, the particulate catalyst in the individual catalyst zones in each case comprises inert ceramic supports and a layer comprising catalytically active metal oxides which has been applied thereto in a fluidized bed with the aid of suitable binders.

In the following, the catalyst zone positioned nearest the gas inlet which is used in the process of the invention for improving the catalysts will be referred to as "upstream catalyst zone of the improved catalyst". In general, the expressions upstream (first), second, third or fourth catalyst zone are based, unless indicated otherwise, on the (improved) catalyst of the invention, and are used as follows in the context of the present invention: the upstream catalyst zone is the catalyst zone of the improved catalyst nearest the gas inlet. In the direction of the gas outlet, at least two further catalyst zones are present in the improved catalyst and these are referred to as second, third or, if present, fourth catalyst zone. The third catalyst zone is located closer to the gas outlet than the second catalyst zone. The individual catalyst zones can be introduced with or without mixing in the interface regions in order to obtain the (multizone) catalyst.

In a preferred embodiment according to the invention, the activity of the third catalyst zone is higher than that of the second catalyst zone in the improved catalyst. Furthermore, the activity of a fourth catalyst zone, if present, is preferably higher than that of the third catalyst zone in the improved catalyst. If a fifth catalyst zone is present, its activity is once again preferably higher than the activity of the fourth catalyst zone. It has also been found that it is particularly advantageous in terms of the performance and life of the catalyst for the activity to increase continuously (i.e. from catalyst zone to catalyst zone) from the 2nd zone to the outlet end for the reaction gas mixture, i.e. to the last catalyst zone, in the improved catalyst.

According to the invention, the activity of the upstream catalyst zone can be made higher than the activity of the subsequent second catalyst zone by any means with which those skilled in the art are familiar.

In a preferred embodiment according to the invention, the increased activity in the upstream catalyst zone can be achieved by, for example:

a higher content of active composition than in the 2nd zone a higher BET surface area (in particular of the $TiO_2$ used) than in the 2nd zone a higher vanadium content than in the 2nd zone a lower Cs content than in the 2nd zone a lower Sb content than in the 2nd zone an increase in the bulk density in the upstream catalyst zone, e.g. by use of a different (ring) geometry of the inert shaped body used;

the presence of or a larger amount of other activity-increasing promoters compared to the second catalyst zone;

the absence of or a smaller amount of activity-damping promoters compared to the second catalyst zone;

or combinations of two or more of the above measures.

Particular preference is given to the upstream catalyst zone having a higher active composition content and/or a higher BET surface area compared to the second catalyst zone. Since the BET surface area of the catalyst zone depends first and foremost on the BET surface area of the $TiO_2$ used, a preferred embodiment according to the invention provides for the BET surface area of the $TiO_2$ in the upstream catalyst zone to be higher than the BET surface area of the $TiO_2$ in the second catalyst zone.

The above measures for producing an increased activity of the first catalyst zone compared to the second catalyst zone can naturally also be used for the preferred setting of the activities of the subsequent catalyst zones (e.g. the third and fourth catalyst zones).

In a preferred embodiment according to the invention, the activity of the upstream catalyst zone is at least 5%, in particular at least 10%, preferably at least 20%, particularly preferably at least 30%, higher than the activity of the subsequent second catalyst zone. A method of determining or comparing the activity of catalysts (catalyst zones) is indicated below in the method part.

The composition of the second and subsequent catalyst zones of the starting catalyst can preferably remain unaltered. The length of the third and any subsequent catalyst zones of the starting catalyst can also preferably remain unaltered.

The second catalyst zone is preferably the least active catalyst zone in the total catalyst according to the invention.

According to the invention, the length of the upstream catalyst zone (1st zone) is preferably such that the hot spot occurs in the subsequent second catalyst zone (2nd zone) and not in the upstream catalyst zone itself under the desired reaction conditions. For this reason, a preferred length in the case of customary reactor tubes is 20-70 cm, particularly preferably 30-60 cm. Here, the customary length of the reactor tubes is from about 2.5 to 3.5 m. The length of the upstream catalyst zone is influenced not only by the volume flow and the loading but also, in particular by the axial temperature gradient in the surrounding coolant (salt bath). In the case of a high axial temperature gradient which occurs when coolant circulation is poor, the temperature of the coolant at the reactor inlet is up to 10° C. higher than at the reactor outlet. In this case, the length of the upstream catalyst zone is made shorter and its activity is made more moderate than in the case of a small axial temperature gradient in the coolant.

In a further, preferred embodiment according to the invention, the individual catalyst zones each have at least titanium and preferably also vanadium in the active composition. It has also been found that particularly good results can be achieved in the preparation of PA when the vanadium content of the active composition in the upstream catalyst zone, calculated as $V_2O_5$, is more than 4% by weight, in particular more than 5% by weight. Preference is also given to Cs and/or Sb being present in the catalyst zones. In a particularly preferred embodiment according to the invention, at least the second catalyst zone contains Cs, with the first (upstream) catalyst zone preferably having a lower Cs content (or containing no Cs at all). It has been found that the interplay of the upstream catalyst zone having a desired high reaction rate for the primary conversion of the o-xylene and/or naphthalene, directly at the beginning of the bed at the gas inlet end, and the second catalyst zone having an early positioning of the hot spot relatively near to the reactor inlet can be brought about particularly well in this way.

In addition, the individual catalyst zones preferably contain no molybdenum and/or tungsten, in particular not in an atomic ratio to vanadium in the range from 0.01 to 2. In a preferred embodiment, no Ni or Co are used in the catalysts employed either. In a preferred embodiment, the Na content of the active composition is less than 500 ppm, in particular less than 450 ppm.

The composition ranges of the catalysts (active composition) used in the individual zones are preferably as follows:

| Composition | Range |
| --- | --- |
| $V_2O_5$/% by wt. | 1-25 |
| $Sb_2O_3$/% by wt. | 0-4 |
| Cs/% by wt. | 0-1 |
| P/% by wt. | 0-2 |
| BET $TiO_2$/(m$^2$/g) | 10 to 50 |
| Proportion of AC/% by wt. | 4-20, preferably 4-15 |

Apart from the above components, the remainder of the active composition comprises at least 90% by weight, preferably at least 95% by weight, more preferably at least 98% by weight, in particular at least 99% by weight, more preferably at least 99.5% by weight, in particular 100% by weight of $TiO_2$. It has also been found in the context of the present invention that particularly advantageous catalysts can, in one embodiment, be produced when the active composition content decreases from the second catalyst zone to the catalyst zone nearest the gas outlet. In a preferred embodiment, the second catalyst zone has an active composition content of from about 6 to 12% by weight, in particular from about 6 to 11% by weight, the third catalyst zone has an active composition content of from about 5 to 11% by weight, in particular from about 6 to 10% by weight, and the fourth catalyst zone (if present) has an active composition content of from about 4 to 10% by weight, in particular from about 5 to 9% by weight. However, catalysts in which the active composition content remains constant or increases from the 2nd zone to the last zone, i.e.:

Active composition content$_{2nd\ zone}$ ≦ active composition content$_{3rd\ zone}$ ≦ ... ≦ active composition content$_{last\ zone}$;

are also possible in principle.

In an advantageous embodiment, at least the active composition content of the last zone is higher than that of the 2nd zone.

In a particularly preferred embodiment according to the invention, the catalyst according to the invention of the upstream catalyst zone has an active composition content of from about 6 to 20% by weight, preferably from about 7 to 15% by weight.

In a particularly preferred embodiment according to the invention, the catalyst of the invention has four catalyst zones. The fourth catalyst zone is then at the gas outlet end. However, the presence of additional catalyst zones in a downstream direction is not ruled out. For example, in an embodiment according to the invention, the fourth catalyst zone as defined herein can be followed by a fifth catalyst zone. Independently of this, the use of a finishing reactor as described, for example, in DE-A-198 07 018 or DE-A-20 05 969 is also possible in the preparation of phthalic acid.

In a preferred embodiment according to the invention, the BET surface area of the $TiO_2$ used increases from the second catalyst zone to the catalyst zone nearest the gas outlet. In other words, preference is given to the BET surface area of the $TiO_2$ used in the second catalyst zone being lower than the BET surface area of the $TiO_2$ used in the catalyst zone nearest the gas outlet (last catalyst zone). Preferred ranges for the BET surface area of the $TiO_2$ are from 15 to 25 $m^2/g$ for the middle catalyst zones and from 15 to 45 $m^2/g$ for the catalyst zone nearest the gas outlet (last catalyst zone).

Particularly advantageous catalysts are also obtained when the BET surface areas of the $TiO_2$ of the middle catalyst zones are identical while the BET surface area of the $TiO_2$ in the last catalyst zone is in comparison greater. The BET surface area of the $TiO_2$ of the upstream catalyst zone is preferably greater than or equal to the BET surface area of the $TiO_2$ of the second catalyst zone or the middle catalyst zones and is in particular in the range from about 15 to 45 $m^2/g$. In an embodiment according to the invention, the BET surface area of the $TiO_2$ used is as follows:

$BET_{TiO2, 2nd\ zone} \leqq BET_{TiO2, 3rd\ zone} \leqq \ldots \leqq BET_{TiO2, last\ zone}$. Even greater preference is given to $BET_{TiO2,\ 1st\ zone} \geqq BET_{TiO2, 2nd\ zone}$.

The temperature management in the gas-phase oxidation of o-xylene to phthalic anhydride is adequately known to a person skilled in the art from the prior art, and reference may be made, for example, to DE 100 40 827 A1.

When the catalyst of the invention is used for preparing phthalic anhydride, it is usual practice to pass a mixture of a gas containing molecular oxygen, for example air, and the starting material to be oxidized (in particular o-xylene and/or naphthalene) through a fixed-bed reactor, in particular a shell-and-tube reactor which can comprise a multiplicity of parallel tubes. A bed of at least one catalyst is present in each of the reactor tubes. The advantages of a bed composed of a plurality of (different) catalyst zones have been discussed above.

When the catalysts of the invention are employed for preparing phthalic anhydride by gas-phase oxidation of o-xylene and/or naphthalene, it has surprisingly been found that use of the catalysts of the invention result in very good PA yields with very low proportions of phthalide and a position of the hot spot close to the reactor inlet, which makes an improved operating life of the catalyst possible.

In a preferred embodiment according to the invention, the $TiO_2$ used (usually in the anatase form) has a BET surface area of at least 15 $m^2/g$, preferably from 15 to 60 $m^2/g$, in particular from about 15 to 45 $m^2/g$ and particularly preferably from 15 to 40 $m^2/g$. Furthermore, preference is given to at least 30%, in particular at least 40%, and up to 80%, preferably up to 75%, in particular up to 70%, of the total pore volume of the $TiO_2$ being formed by pores having a radius of from 60 to 400 nm. The determination of the pore volumes and proportions reported here is carried out, unless indicated otherwise, by means of mercury porosimetry (in accordance with DIN 66133). The figure given for the total pore volume in the present description is in each case based on the total pore volume measured by means of mercury porosimetry in the pore radius range from 7500 to 3.7 nm. Pores having a radius of more than 400 nm preferably make up less than about 30%, in particular less than about 22%, particularly preferably less than 20%, of the total pore volume of the $TiO_2$ used. Furthermore, preference is given to from about 50 to 75%, in particular from about 50 to 70%, particularly preferably from 50 to 65%, of the total pore volume of the $TiO_2$ being formed by pores having a radius of from 60 to 400 nm and preferably from about 15 to 25% of the total pore volume being formed by pores having a radius of more than 400 nm. With regard to the smaller pore radii, it is preferred that less than 30%, in particular less than 20%, of the total pore volume of the $TiO_2$ is formed by pores having a radius of from 3.7 to 60 nm. A particularly preferred range for this pore size is from about 10 to 30% of the total pore volume, in particular from 12 to 20%.

In a further preferred embodiment, the $TiO_2$ used has the following particle size distribution: The $D_{10}$ is preferably 0.5 µm or less; the $D_{50}$ (i.e. the value at which half the particles have a larger diameter and half the particles have a smaller diameter) is preferably 1.5 µm or less; the $D_{90}$ is preferably 4 µm or less. The $D_{90}$ of the $TiO_2$ used is preferably in the range from about 0.5 to 20 µm, in particular from about 1 to 10 µm, particularly preferably from about 2 to 5 µm. In electron micrographs, the $TiO_2$ used according to the invention preferably has an open-pored, sponge-like structure in which more than 30%, in particular more than 50%, of the primary particles or crystallites are agglomerated to form open-pored agglomerates. It is assumed, without the invention being restricted to this assumption, that this particular structure of the $TiO_2$ used, which is reflected in the pore radius distribution, creates particularly favourable reaction conditions for the gas-phase oxidation.

In principle, another titanium dioxide having a different specification than that described above, i.e. a different BET surface area, porosimetry and/or particle size distribution, can also be used in the catalyst of the invention. According to the invention, it is particularly preferred that at least 50%, in particular at least 75%, particularly preferably all, of the $TiO_2$ used has a BET surface area and porosimetry as defined herein and preferably also has the particle size distribution described. Blends of different $TiO_2$ materials can also be used.

Depending on the envisaged use of the catalyst of the invention, the customary components known to those skilled in the art can be present in the active composition of the catalyst in addition to $TiO_2$. The shape of the catalysts and its homogeneous or heterogeneous structure are in principle also not subject to any restrictions for the purposes of the present invention and can have any variant which is known to those skilled in the art and appears suitable for the respective application.

Coated catalysts have been found to be particularly useful for the preparation of phthalic anhydride. Here, a support which is inert under the reaction conditions, for example silica ($SiO_2$), porcelain, magnesium oxide, tin dioxide, silicon carbide, rutile, alumina ($Al_2O_3$), aluminium silicate, magnesium silicate (steatite), zirconium silicate or cerium silicate or mixtures of the above materials, is used. The support can, for example, have the shape of rings, spheres, shells or hollow cylinders. The catalytically active composition is applied thereto in comparatively thin layers (coatings). It is also possible for two or more layers of a catalytically active composition having the same or different composition to be applied.

With regard to the further components of the catalytically active composition of the catalyst of the invention (in addition to $TiO_2$), reference may basically be made to the compositions or components which are described in the relevant prior art and with which those skilled in the art are familiar. These are mainly catalyst systems in which oxides of vanadium are present in addition to titanium oxide(s). Such catalysts are described, for example, in EP 0 964 744 B1 whose relevant disclosure is hereby expressly incorporated by reference into the present description. In many cases, it can be preferable to use a $V_2O_5$ material having quite a small particle size for the individual catalyst zones of the catalyst of the invention in order to aid spraying onto the $TiO_2$. For example, at least 90% of the $V_2O_5$ particles used can have a diameter of 20 μm or less. On this subject, reference may be made, for example, to DE 10344846 A1.

In particular, a series of promoters to increase the productivity of the catalysts are described in the prior art and these can likewise be used in the catalyst of the invention. They include, inter alia, the alkali metals and alkaline earth metals, thallium, antimony, phosphorus, iron, niobium, cobalt, molybdenum, silver, tungsten, tin, lead and/or bismuth and also mixtures of two or more of the above components. In a preferred embodiment according to the invention, the catalysts used according to the invention thus contain one or more of the above promoters. For example, DE 21 59 441 A describes a catalyst which comprises titanium dioxide in the anatase modification together with from 1 to 30% by weight of vanadium pentoxide and zirconium dioxide. A listing of suitable promoters may also be found in WO2004/103561, page 5, lines 29 to 37, which is likewise incorporated by reference. The individual promoters enable the activity and selectivity of the catalysts to be influenced, in particular by reducing or increasing the activity. Selectivity-controlling promoters include, for example, the alkali metal oxides and oxidic phosphorus compounds, in particular phosphorus pentoxide. In a preferred embodiment, the upstream catalyst zone and preferably also the second catalyst zone contain(s) no phosphorus. It has been found that a high activity can be achieved in this way, with the selectivity in the subsequent catalyst zones (3rd and further zone(s)) being able to be set advantageously by, for example, the presence of phosphorus. In some cases it can be advantageous for only the last zone to contain phosphorus. In a further preferred embodiment, the ratio of vanadium, calculated as $V_2O_5$, to antimony, calculated as $Sb_2O_3$, in the catalyst of the upstream zone and/or in the catalyst of the 2nd zone is from about 3.5:1 to 5:1, as described, for example, in DE 103 23 461 A.

In a further preferred embodiment, the alkali metal content, preferably the Cs content, of the catalyst of the invention remains constant or decreases from the 2nd zone to the last zone (at the gas outlet end). In other words:

Cs content$_{2nd\ zone}$ ≧ Cs content$_{3rd\ zone}$ ≧ ... ≧ Cs content$_{last\ zone}$. Particular preference is given to the last catalyst zone containing no Cs.

Numerous suitable methods of producing the catalysts of the invention are described in the prior art, so that a detailed presentation here is basically unnecessary. For the production of coated catalysts, reference may be made, for example, to the process described in DE-A-16 42 938 or DE-A 17 69 998, in which a solution or suspension of the components of the catalytically active composition and/or their precursor compounds in water and/or an organic solvent (frequently referred to as "slurry") is sprayed onto the support material in a heated coating drum at elevated temperature until the desired content of catalytically active composition, based on the total weight of the catalyst, has been achieved. The application of the catalytically active composition to the inert support (coating process) can also be carried out in fluidized-bed coaters as described in DE 21 06 796.

Coated catalysts are preferably produced by applying a thin layer of from 50 to 500 μm of the active component to an inert support (cf. U.S. Pat. No. 2,035,606). Spheres or hollow cylinders have been found to be particularly useful as supports. These shaped bodies give a high packing density with a low pressure drop and reduce the risk of formation of packing defects when the catalyst is introduced into the reaction tubes.

The molten and sintered shaped bodies have to be heat-resistant within the temperature range of the reaction which occurs. As indicated above, possibilities are, for example, silicon carbide, steatite, silica, porcelain, $SiO_2$, $Al_2O_3$ or alumina.

The advantage of carrying out the coating of support bodies in a fluidized bed is the high uniformity of the layer thickness which plays a critical role in the catalytic performance of the catalyst. A particularly uniform coating is obtained by spraying a suspension or solution of the active components onto the heated support at from 80 to 200° C. in a fluidized bed, for example as described in DE 12 80 756, DE 198 28 583 or DE 197 09 589. In contrast to coating in a coating drum, when hollow cylinders are used as supports, the inside of the hollow cylinder can also be coated uniformly in the fluidized-bed processes described. Among the fluidized-bed processes described above, the process of DE 197 09 589 is particularly advantageous since the predominantly horizontal, circular motion of the supports enables not only uniform coating but also low abrasion of apparatus components to be achieved.

In the coating procedure, the aqueous solution or suspension of the active components and an organic binder, preferably a copolymer of vinyl acetate-vinyl laurate, vinyl acetate-ethylene or styrene-acrylate, is sprayed by means of one or more nozzles onto the heated, fluidized support. It is particularly advantageous to introduce the spray liquid at the point of greatest product velocity where the sprayed material can be distributed uniformly in the bed. The spraying procedure is continued until either the suspension has been used up or the required amount of active components has been applied to the support.

In a particularly preferred embodiment according to the invention, the catalytically active composition of the catalyst of the invention is applied in a moving bed or fluidized bed with the aid of suitable binders so that a coated catalyst is produced. Suitable binders encompass organic binders with which those skilled in the art are familiar, preferably copolymers, advantageously in the form of an aqueous dispersion, of vinyl acetate-vinyl laurate, vinyl acetate-acrylate, styrene-acrylate, vinyl acetate-maleate and vinyl acetate-ethylene. Particular preference is given to using an organic polymeric or copolymeric adhesive, in particular a vinyl acetate copolymer adhesive, as binder. The binder used is added to the catalytically active composition in customary amounts, for example from about 10 to 20% by weight, based on the solids content of the catalytically active composition. For example, reference may be made to EP 744 214. If the application of the catalytically active composition is carried out at elevated temperatures of about 150° C., application to the support without organic binders is also possible, as is known from the prior art. Coating temperatures which can be employed when using the abovementioned binders are, according to DE 21 06 796, in the range from, for example, about 50 to 450° C. The binders used burn out within a short time when the catalyst is heated during start-up of the charged reactor. The binders serve first and foremost to strengthen the adhesion of the catalytically active composition to the support and to reduce attrition during transport and charging of the catalyst.

Further possible processes for producing coated catalysts for the catalytic gas-phase oxidation of aromatic hydrocarbons to carboxylic acids and/or carboxylic anhydrides have been described, for example, in WO 98/00778 and EP-A 714 700. According to this, a powder is firstly produced from a solution and/or suspension of the catalytically active metal oxides and/or their precursor compounds, if appropriate in the presence of auxiliaries for catalyst production, and this is subsequently, in order to produce the catalyst, applied in the form of a coating to the support, if appropriate after conditioning and if appropriate after heat treatment to produce the catalytically active metal oxides, and the support which has been coated in this way is subjected to heat treatment to produce the catalytically active metal oxides or a treatment to remove volatile constituents.

Suitable conditions for carrying out a process for the preparation of phthalic anhydride from o-xylene and/or naphthalene are likewise known to those skilled in the art from the prior art. In particular, reference may be made to the summary presentation in K. Towae, W. Enke, R. Jäckh, N. Bhargana "Phthalic Acid and Derivatives" in Ullmann's Encyclopedia of Industrial Chemistry Vol. A. 20, 1992, 181, and this is hereby incorporated by reference. For example, the boundary conditions known from the above reference WO-A 98/37967 or WO 99/61433 can be selected for steady-state operation of the oxidation.

For this purpose, the catalysts are firstly introduced into the reaction tubes of the reactor, which are thermostatted from the outside to the reaction temperature, for example by means of salt melts. The reaction gas is passed at temperatures of generally from 300 to 450° C., preferably from 320 to 420° C. and particularly preferably from 340 to 400° C., and a gauge pressure of generally from 0.1 to 2.5 bar, preferably from 0.3 to 1.5 bar, over the catalyst bed prepared in this way at a space velocity of generally from 750 to 5000 $h^{-1}$.

The reaction gas passed over the catalyst is generally produced by mixing a gas containing molecular oxygen, which can comprise oxygen together with suitable reaction moderators and/or diluents such as steam, carbon dioxide and/or nitrogen, with the aromatic hydrocarbon to be oxidized. The gas containing molecular oxygen can generally comprise from 1 to 100 mol %, preferably from 2 to 50 mol % and particularly preferably from 10 to 30 mol %, of oxygen, from 0 to 30 mol %, preferably from 0 to 10 mol %, of water vapour and from 0 to 50 mol %, preferably from 0 to 1 mol %, of carbon dioxide, with the balance being nitrogen. To produce the reaction gas, the gas containing the molecular oxygen is generally admixed with from 30 to 150 g of the aromatic hydrocarbon to be oxidized per standard $m^3$ of gas.

In a particularly preferred embodiment according to the invention, the active composition (catalytically active composition) of the catalyst of the upstream catalyst zone comprises from 5 to 16% by weight of $V_2O_5$, from 0 to 5% by weight of $Sb_2O_3$, from 0.2 to 0.75% by weight of Cs, 0-1% by weight of P and from 0 to 3% by weight of $Nb_2O_5$. The remainder of the active composition comprises at least 90% by weight, preferably at least 95% by weight, more preferably at least 98% by weight, in particular at least 99% by weight, more preferably at least 99.5% by weight, in particular 100% by weight, of $TiO_2$. In a particularly preferred embodiment according to the invention, the BET surface area of the $TiO_2$ is from 15 to about 45 $m^2/g$. Furthermore, preference is given to such an upstream catalyst zone making up 5-25%, particularly preferably 10-25%, of the total length of all catalyst zones present (total length of the catalyst bed present).

In a particularly preferred embodiment according to the invention, the active composition of the catalyst of the second catalyst zone comprises from 5 to 25% by weight of $V_2O_5$, from 0 to 5% by weight of $Sb_2O_3$, from 0.2 to 0.75% by weight of Cs, 0-1% by weight of P and from 0 to 2% by weight of $Nb_2O_5$. The remainder of the active composition comprises at least 90% by weight, preferably at least 95% by weight, more preferably at least 98% by weight, in particular at least 99% by weight, more preferably at least 99.5% by weight, in particular 100% by weight, of $TiO_2$. In a particularly preferred embodiment according to the invention, the BET surface area of the $TiO_2$ is from 15 to about 25 $m^2/g$. Furthermore, preference is given to such a second catalyst zone making up from about 15 to 60%, in particular from 20 to 60% or from 20 to 50%, of the total length of all catalyst zones present (total length of the catalyst bed present).

In a particularly preferred embodiment according to the invention, the active composition of the catalyst of the third catalyst zone comprises from 5 to 15% by weight of $V_2O_5$, from 0 to 4% by weight of $Sb_2O_3$, from 0.05 to 0.5% by weight of Cs, 0-1% by weight of P and from 0 to 2% by weight of $Nb_2O_5$. The remainder of the active composition comprises at least 90% by weight, preferably at least 95% by weight, more preferably at least 98% by weight, in particular at least 99% by weight, more preferably at least 99.5% by weight, in particular 100% by weight, of $TiO_2$. The $TiO_2$ preferably has a BET surface area in the range from about 15 to 25 $m^2/g$. Furthermore, preference is given to this third zone making up from about 10 to 30% of the total length of all catalyst zones present, in particular if the third zone is followed by at least one further catalyst zone. If the third zone is the last zone, i.e. the zone nearest the reactor outlet, the 3rd zone preferably makes up 20-50% of the total length.

In a particularly preferred embodiment according to the invention, the active composition of the catalyst of the fourth catalyst zone comprises from 5 to 25% by weight of $V_2O_5$, from 0 to 5% by weight of $Sb_2O_3$, from 0 to 0.2% by weight of Cs, 0-2% by weight of P and from 0 to 1% by weight of $Nb_2O_5$. The remainder of the active composition comprises at least 90% by weight, preferably at least 95% by weight, more preferably at least 98% by weight, in particular at least 99% by weight, more preferably at least 99.5% by weight, in particular 100% by weight, of $TiO_2$. If the fourth zone represents the catalyst zone nearest the gas outlet of the reactor (last catalyst zone), preference is given to a BET surface area of the $TiO_2$ which is somewhat higher than that of the zones closer to the gas inlet, in particular in the range from about 15 to about 45 $m^2/g$. Furthermore, preference is given to such a fourth catalyst zone making up from about 10 to 50%, particularly preferably from 10 to 40%, of the total length of all catalyst zones present. A fifth catalyst zone is then generally not necessary, but is possible.

It has also been found that, in a preferred embodiment, catalysts according to the invention which have no phosphorus in the catalytically active composition in the middle catalyst zone and, if appropriate, in the upstream catalyst zone, display particularly good activities combined with a very high selectivity. Furthermore, preference is given to at least 0.05% by weight of the catalytically active composition in the upstream catalyst zone and the middle catalyst zones being formed by at least one alkali metal, calculated as alkali metal(s). Caesium is particularly preferred as alkali metal.

The catalysts of the invention can be heat treated or calcined (conditioned) in a customary manner before use. It has here been found to be advantageous for the catalyst to be calcined for at least 24 hours at least 390° C., in particular from 24 to 72 hours at $\geq$400° C., in an $O_2$-containing gas, in particular in air. The temperature should preferably not exceed 500° C., in particular 470° C. However, other calcination conditions which appear suitable to a person skilled in the art are not ruled out in principle.

According to a further aspect, the present invention provides a process for producing a catalyst as described herein, which comprises the following steps:

a. provision of a catalytically active composition as defined herein, b. provision of an inert support, in particular an inert support shaped body;

c. application of the catalytically active composition to the inert support, in particular in a fluidized bed or a moving bed.

The individual catalysts are subsequently introduced in the desired order as catalyst zones into the reactor in order to obtain the improved multizone catalyst.

According to a further aspect, the invention also provides a process for the preparation of phthalic anhydride by gas-phase oxidation of o-xylene and/or naphthalene, in which a three-zone or multizone catalyst as defined in the above description is used. In this process, a gaseous stream comprising o-xylene and/or naphthalene and also molecular oxygen is generally passed at elevated temperature, in particular from about 250 to 490° C., over a three-zone or multizone catalyst as defined in the preceding claims.

According to a further aspect, the present invention finally also provides for the use of an improved catalyst as defined herein for the preparation of phthalic anhydride by gas-phase oxidation of o-xylene and/or naphthalene.

The process of the invention for improving or optimizing a catalyst can naturally also be carried out by, starting out from the formulation of the starting catalyst known from the prior art, straightaway producing a fresh bed of the improved catalyst including the upstream catalyst zone, with the length of the upstream catalyst zone which replaces part of the first catalyst zone of the starting catalyst formulation being selected as indicated herein.

If, in a possible embodiment according to the invention, the precise position of the hot spot in the first catalyst zone of the starting catalyst is firstly to be determined in test operation of the starting catalyst according to the prior art, it is in practice not simple and thus also generally not advisable to replace part of the first catalyst zone by the upstream catalyst zone in the used starting catalyst itself. In general, it will be simpler to carry out and preferred to produce a fresh catalyst bed on the basis of the results of test operation using the starting catalyst, with the part calculated as described herein of the first catalyst zone of the starting catalyst in the direction of the gas inlet being replaced by the upstream catalyst zone having a high activity in the catalyst formulation.

According to a further aspect, the present invention provides for the use of an upstream catalyst zone for improving a catalyst having two or more different catalyst zones (starting catalyst) for the partial oxidation of hydrocarbons, in particular for the preparation of phthalic anhydride by gas-phase oxidation of o-xylene and/or naphthalene, wherein the activity of the upstream catalyst zone is higher than the activity of the first catalyst zone of the starting catalyst.

Methods

The following methods are used for determining the parameters of the catalysts according to the invention:

1. BET Surface Area:

The determination is carried out by the BET method in accordance with DIN 66131; the BET method is also published in J. Am. Chem. Soc. 60, 309 (1938).

2. Pore Radius Distribution:

The determination of the pore radius distribution of the $TiO_2$ used was carried out by mercury porosimetry in accordance with DIN 66133; maximum pressure: 2,000 bar, Porosimeter 4000 (from Porotec, Germany), in conformity with the manufacturer's instructions.

3. Particle Sizes:

The determination of the particle sizes was carried out by the laser scattering method using a Fritsch Particle Sizer Analysette 22 Economy (from Fritsch, Germany) in conformity with the manufacturer's instructions, including sample pretreatment: the sample is homogenized in deionized water without addition of auxiliaries and treated with ultrasound for 5 minutes.

The determination of the BET surface area, the pore radius distribution or the pore volume and the particle size distribution was in the case of titanium dioxide in each case carried out on the uncalcined material dried at 150° C. under reduced pressure.

The figures quoted in the present description for the BET surface areas of the catalysts or catalyst zones also refer to the BET surface areas of the $TiO_2$ material used in each case (dried at 150° C. under reduced pressure, uncalcined, cf. above).

In general, the BET surface of the catalyst is determined by the BET surface area of the $TiO_2$ used, with the addition of further catalytically active components changing the BET surface area to a certain extent. A person skilled in the art will know this.

The active composition content (proportion of catalytically active composition without binder) is in each case the proportion (in % by weight) of the total weight of the catalyst including support which is made up by the catalytically active composition in the respective catalyst zone, measured after conditioning at 400° C. for 4 hours in air.

4. Catalyst Activity:

For the purposes of the invention, the activity of the catalyst in a catalyst zone is the ability of the catalyst to react the starting material used within a defined volume (=balance space), for example a reaction tube of defined length and internal diameter (e.g. 25 mm internal diameter, 1 m length), under prescribed reaction conditions (temperature, pressure, concentration, residence time). The catalyst under consideration accordingly has a higher activity than another catalyst when it achieves a higher conversion of starting material in this prescribed volume under in each case identical reaction conditions. In the case of o-xylene or naphthalene as starting material, the catalyst activity is thus given by the magnitude of the conversion of o-xylene or naphthalene into the oxidation products. The cause of a higher catalyst activity can be either an optimized nature/quality of the active sites for the desired reaction (cf., for example, "turnover frequency") or an increased number of active sites in the same balance space, which is the case when, for example, a larger mass of catalyst having otherwise identical properties is present in the balance space.

Operational Quantification of the Activity:

According to the invention, the activity of the 1st zone is higher than that of the 2nd zone. This means firstly that, in accordance with the present exposition, the conversion of starting material at the end of a reaction space (=reaction tube of defined length and internal diameter, e.g. 25 mm internal diameter, 1 m length) which is charged with "zone 1 catalyst" and through which the feed mixture flows is higher than in an otherwise identical comparative experiment in which the identical reaction space has been filled with "zone 2 catalyst".

Such a test is advantageously carried out using conditions within the following ranges:

| | |
|---|---|
| Length of reaction tube: | 1 m |
| Internal diameter of reaction tube: | 25 mm |
| Temperature of cooling medium: | 380-420° C. |
| Pressure: | 1-1.5 bar absolute |
| o-Xylene loading in feed mixture: | 60 g of o-xylene/ standard $m^3$ of air |

The activity of the first catalyst zone compared to the activity of the second catalyst zone can then be quantified as follows with the aid of the following definition according to the invention of a "catalyst having a 10% higher activity" used for zone 1 compared to a catalyst used for zone 2:

The feed mixture is passed through the comparative catalyst (=zone 2 catalyst having the intended composition) under the abovementioned conditions, with the total volume flow through the reaction tube being set so that the o-xylene conversion after passage through the reaction space is very close to 50%.

In a second experiment, the same reaction volume is filled with zone 1 (test) catalyst which differs from the zone 2 catalyst only in that the active composition content is 10% higher. Thus, 10% more active composition is present in the reaction volume than in the case of the comparative catalyst. The o-xylene conversion after passage through the reaction space filled with zone 1 catalyst is then determined under identical reaction conditions. This is higher than that obtained using the comparative catalyst, i.e. higher than 50%. The difference between the o-xylene conversion obtained in this way and the 50% conversion obtained using the comparative catalyst is used as a relative figure corresponding to a 10% increase in activity. The change made to the catalyst to achieve such an effect is immaterial. Accordingly, a catalyst which differs from the intended zone 2 catalyst only in that the active composition content is 20% higher can, for example, be used to determine a figure for a 20% higher activity of the catalyst, etc.

In the present description, the hot spot is the maximum temperature measured in the entire catalyst bed. Furthermore, there are also (secondary) hot spots, i.e. maximum temperatures, in the further catalyst zones under consideration.

The invention is illustrated by the following nonlimiting examples:

EXAMPLES

Example

Starting Catalyst:

As starting catalyst, a 3-zone catalyst system having the composition and zone length shown below is introduced into a tube reactor which has an internal diameter of 25 mm and is cooled by means of a salt bath. A 3 mm thermocouple sheath having an installed movable element was arranged centrally in the reaction tube to measure the temperature. 4 standard $m^3/h$ of air having a loading of 30-100 g of o-xylene/standard $m^3$ of air (o-xylene purity>99%) were passed through the tube from the top downwards at a total pressure of about 1450 mbar.

At a loading of 60-65 g of o-xylene/standard $m^3$ of air, and a salt bath temperature of from 370 to 375° C., the hot spot was measured in zone 1 at a position of 90-100 cm (from the beginning of the bed in the direction of the reactor outlet).

| Composition | Zone 1 Length: 150 cm | Zone 2 Length: 60 cm | Zone 3 Length: 80 cm |
|---|---|---|---|
| $V_2O_5$/% by wt. | 7.5 | 7.5 | 7.5 |
| $Sb_2O_3$/% by wt. | 3.2 | 3.2 | 3.2 |
| Cs/% by wt. | 0.4 | 0.2 | 0.1 |
| P/% by wt. | 0.2 | 0.2 | 0.2 |
| $TiO_2$/% by wt. | balance to 100% | balance to 100% | balance to 100% |
| BET of $TiO_2/(m^2/g)$ | 20 | 20 | 30 |
| Proportion of AC/% by weight | 8.0 | 7.5 | 7.5 |

Catalyst According to the Invention (Improved Catalyst):

On the basis of the results regarding the position of the hot spot (A=90-100 cm) obtained using the starting catalyst, an improved catalyst was then produced as follows:

The above composition of the 3-zone starting catalyst system was modified by replacing 50 cm of zone 1 of the starting catalyst (from the gas inlet end or beginning of the catalyst bed) by a more active upstream catalyst zone. The composition and zone lengths of the improved 4-zone catalyst system according to the invention can be seen from the following table. Here, zone 1 corresponds to the upstream catalyst zone according to the invention; the upstream catalyst zone according to the invention; the composition of zone 2 corresponds (apart from the zone length) to that of zone 1 of the starting catalyst. The composition and zone lengths of zones 3 and 4 correspond to those of zones 2 and 3, respectively, of the starting catalyst. The 4-zone catalyst according to the invention having the composition and zone lengths shown below was introduced into a tube reactor which had an internal diameter of 25 mm and was cooled by means of a salt bath. A 3 mm thermocouple sheath having an installed movable element was arranged centrally in the reaction tube to measure the temperature. 4 standard $m^3/h$ of air having a loading of 30-100 g of o-xylene/standard $m^3$ of air (o-xylene purity>99%) were passed through the tube from the top downwards at a total pressure of about 1450 mbar.

At a loading of 60-65 g of o-xylene/standard $m^3$ of air, and a salt bath temperature of from 365 to 375° C., the above-described hot spot was measured at a position of 75-85 cm (from the beginning of the bed in the direction of the reactor outlet).

| Composition | Zone 1 Length: 50 cm | Zone 2 Length: 100 cm | Zone 3 Length: 60 cm | Zone 4 Length: 80 cm |
|---|---|---|---|---|
| $V_2O_5$/% by weight | 8.0 | 7.5 | 7.5 | 7.5 |
| $Sb_2O_3$/% by weight | 3.2 | 3.2 | 3.2 | 3.2 |
| Cs/% by weight | 0.4 | 0.4 | 0.2 | 0.1 |
| P/% by weight | 0.2 | 0.2 | 0.2 | 0.2 |
| $TiO_2$/% by weight | balance to 100% | balance to 100% | balance to 100% | balance to 100% |
| BET of $TiO_2/(m^2/g)$ | 20 | 20 | 20 | 30 |
| Proportion of AC/% by weight | 10 | 8 | 7.5 | 7.5 |

The position of the hot spot in the example according to the invention is thus significantly closer to the reactor inlet than in the comparative example.

This leads to the following advantages for the improved catalyst according to the invention, with these applying not only to the specific example but generally for the present invention:

Longer life since the hot spot is located closer to the reactor inlet at the beginning of the reaction and accordingly also as deactivation progresses; in particular it remains longer in the 2nd zone (formerly 1st zone).

A lower content of phthalide in the reaction gas leaving the reactor since the reaction has moved further upstream.

The (secondary) hot spot in the 3rd zone is lower than in the equivalent 2nd zone of the starting catalyst since more o-xylene is reacted in the two preceding zones 1 and 2 than in zone 1 in the starting catalyst.

The invention claimed is:

1. A process for improving or optimizing a catalyst for the preparation of phthalic anhydride by gas-phase oxidation of o-xylene and/or naphthalene, which comprises
    a) providing a starting catalyst comprising at least a first catalyst zone located towards a gas inlet and a second catalyst zone located closer to a gas outlet, with the catalyst of each of the catalyst zones containing an active composition comprising $TiO_2$, which $TiO_2$ has a BET surface area of at least 15 $m^2/g$, and
    b) replacing part of the first catalyst zone located directly at the gas inlet with an upstream catalyst zone of the catalyst having a higher activity than the remaining first catalyst zone in order to provide an improved catalyst.

2. The process according to claim 1,
    wherein the position of the temperature maximum (hot spot) in the first catalyst zone of the starting catalyst is calculated as distance A from a beginning of the first catalyst zone (gas inlet end) during use (operation) of the catalyst; and
    wherein the length of the upstream catalyst zone of the catalyst according to claim 1(b) is less than A and wherein a temperature maximum in the catalyst is located in the first catalyst zone of the starting catalyst but closer to the beginning of the first catalyst zone (gas inlet end) than in the catalyst prior to replacing part of the first catalyst zone with the upstream catalyst zone.

3. The process according to claim 1 characterized in that the starting catalyst further comprises a third catalyst zone which is closer to or at the gas outlet than is the second catalyst zone.

4. The process according to claim 3, wherein the catalyst activity increases from the second to the third catalyst zone in the catalyst.

5. The process according to claim 3 characterized in that the catalyst activity increases from the third to a fourth catalyst zone.

6. The process according to claim 5, characterized in that a total of four catalyst zones are present in the catalyst.

7. The process according to claim 1, characterized in that the length of the upstream catalyst zone is from about 5 to 30%, of the total length of a total catalyst bed in the catalyst.

8. The process according to claim 1, characterized in that the upstream catalyst zone has a characteristic of one or more of the following:
    a. a higher active composition content,
    b. a higher vanadium content,
    c. a $TiO_2$ having a higher BET surface area,
    d. a lower Sb content,
    e. a lower Cs content,
    f. a higher content of promoters which increase the activity,
    g. a higher bulk density, in particular as a result of the use of a different geometry of the shaped bodies, and
    h. a lower content of promoters which lower the activity when compared to the second catalyst zone in the catalyst.

9. The process according to claim 1 characterized in that the catalyst zones comprise coated catalysts wherein the active composition has been applied to an inert support.

10. The process according to claim 1, characterized in that the active composition of the catalyst zones in the catalyst comprise at least:

| Composition | Range |
| --- | --- |
| $V_2O_5$/% by wt. | 1-25 |
| $Sb_2O_3$/% by wt. | 0-4 |
| Cs/% by wt. | 0-1 |
| P/% by wt. | 0-2 | with the remainder of the active composition comprising at least 90% by weight, of $TiO_2$, the BET surface area of the $TiO_2$ is in the range from about 10 to 50 $m^2/g$ and the active composition comprises from about 4 to 20% by weight of the total weight of the catalyst.

11. The process according to claim 1, characterized in that the upstream catalyst zone of the catalyst has an active composition comprising from about 6 to 20% by weight, and the active composition comprises from 5 to 16% by weight of $V_2O_5$, from 0 to 5% by weight of $Sb_2O_3$, from 0.2 to 0.75 % by weight of Cs, 0 - 1% by weight of P and from 0 to 3% by weight of $Nb_2O_5$ and the remainder of the active composition comprises at least 90% by weight, of $TiO_2$.

12. The process according to claim 1, characterized in that the second catalyst zone in the catalyst has an active composition comprising from about 6 to 12% by weight, with the active composition comprising from 5 to 15% by weight of $V_2O_5$, from 0 to 5% by weight of $Sb_2O_3$, from 0.2 to 0.75% by weight of Cs, 0- 1% by weight of P, from 0 to 2% by weight of $Nb_2O_5$ and the remainder of the active composition comprising at least 90% by weight, of TiO2.

13. The process according to claim 3, characterized in that the third catalyst zone in the catalyst has an active composition comprising from about 5 to 11% by weight, with the active composition comprising from 5 to 15% by weight of $V_2O_5$, from 0 to 4% by weight of $Sb_2O_3$, from 0.05 to 0.5% by weight of Cs, 0-1% by weight of P, from 0 to 2% by weight of $Nb_2O_5$ and the remainder of the active composition comprising at least 90% by weight, of TiO2.

14. The process according to claim 5, characterized in that the fourth catalyst zone in the catalyst has an active composition comprising from 5 to 25% by weight of $V_2O_5$, from 0 to 5% by weight of $Sb_2O_3$, from 0 to 0.2% by weight of Cs, from 0 to 2% by weight of P, from 0 to 1% by weight of $Nb_2O_5$ and the remainder of the active composition comprises at least 90% by weight, of TiO2.

15. The process according to claim 5, characterized in that the upstream catalyst zone has an active composition content of from about 7 to 20% by weight,
    the second catalyst zone in the catalyst has an active composition content of from about 7 to 12% by weight, with the active composition content of the second catalyst zone being less than or equal to the active composition content of the first catalyst zone;
    the third catalyst zone in the catalyst has an active composition content in the range from about 6 to 11% by weight, with the active composition content of the third catalyst zone being less than or equal to the active composition content of the second catalyst zone, and
    the fourth catalyst zone in the catalyst has an active composition content in the range from 5 to 10% by weight, with the active composition content of the fourth catalyst zone being less than or equal to the active composition content of the third catalyst zone.

16. The process according to claim 1, characterized in that the BET surface area of the catalyst zone nearest the gas outlet in the catalyst is higher than the BET surface area of the preceding (upstream) catalyst zones.

17. The process according to claim 1, characterized in that the active composition is applied in a moving bed or fluidized bed.

18. The process according to claim 1, characterized in that at least 0.05% by weight of the active composition of at least one catalyst zone in the catalyst comprises at least one alkali metal, calculated as alkali metal(s).

19. The process according to claim 1, characterized in that an organic polymer or copolymer, comprising vinyl acetate copolymer is used as an adhesive for the active composition.

20. The process according to claim 1, characterized in that the catalyst is calcined or conditioned for at least 24 hours at >390° C., in an $O_2$-containing gas.

21. The process according to claim 1, characterized in that niobium is present in the active composition in an amount of from 0.1 to 2% by weight, in at least one catalyst zone in the catalyst.

22. The process according to claim 1, characterized in that the active composition in the catalyst zone in the catalyst closest to the gas outlet further comprises phosphorus.

23. The process according to claim 1, characterized in that the upstream zone has an activity which is at least 5%, higher than that of the subsequent second zone in the catalyst.

24. Improved catalyst obtainable by a process according to claim 1.

25. A process for preparation of phthalic anhydride whereby a gaseous stream comprising o-xylene and/or naphthalene and also molecular oxygen is passed at elevated temperature over the improved catalyst according to claim 24.

* * * * *